United States Patent [19]

Yu et al.

[11] 4,284,630

[45] Aug. 18, 1981

[54] STABILIZED WATER-IN-OIL EMULSIONS

[76] Inventors: Ruey J. Yu, 4 Lindenwold Ave., Ambler, Pa. 19002; Eugene J. Van Scott, 1138 Sewell La., Rydal, Pa. 19046

[21] Appl. No.: 43,266

[22] Filed: May 29, 1979

Related U.S. Application Data

[63] Continuation of Ser. No. 888,938, Mar. 22, 1978, abandoned, which is a continuation-in-part of Ser. No. 852,147, Nov. 16, 1977, abandoned.

[51] Int. Cl.³ .............................................. A61K 31/58
[52] U.S. Cl. .................................... 424/241; 424/243; 424/264; 424/305
[58] Field of Search ................. 424/34, 238, 241, 243, 424/142, 158, 264, 365

[56] References Cited

U.S. PATENT DOCUMENTS

| | | | |
|---|---|---|---|
| 1,384,460 | 12/1920 | Haley | 424/157 |
| 1,999,160 | 4/1935 | Walton | 424/158 |
| 3,019,162 | 1/1962 | Brunner et al. | 424/172 X |
| 3,846,556 | 11/1974 | Handjanine-Vila et al. | 424/365 X |
| 3,914,407 | 10/1975 | Kalopissis et al. | 424/365 X |
| 4,005,191 | 1/1977 | Clark | 424/157 X |
| 4,035,513 | 7/1977 | Kumano | 424/172 X |
| 4,067,975 | 1/1978 | Yu et al. | 424/240 |

FOREIGN PATENT DOCUMENTS

| | | | |
|---|---|---|---|
| 172655 | 12/1920 | United Kingdom | 424/158 |
| 884688 | 12/1961 | United Kingdom | 424/365 |

OTHER PUBLICATIONS

Vitamin E–Miracle or Myth, FDA Consumer, Jul.-Aug. 1973, pp. 24-25.
Caswell–Massey Co. Ltd., "Winter Catalogue 1972/1973", p. 62.
MuCutcheon, "Detergents and Emulsifices 1973 Annual" 1973, p. 154.

*Primary Examiner*—Elbert L. Roberts
*Attorney, Agent, or Firm*—LeBlanc, Nolan, Shur & Nies

[57] ABSTRACT

Stable water-in-oil emulsions useful as vehicles for cosmetics or for therapeutic compositions to be topically applied are disclosed. The emulsions utilize a concentration of from 0.2 to 2% by weight of magnesium oxide or magnesium hydroxide as a stabilizing agent. The stabilizing agent may be admixed with either the oil or the aqueous phase, and use thereof will permit incorporating up to 70% water in the total composition without loss of stability during either prolonged storage, or exposure to freezing and thawing.

34 Claims, No Drawings

STABILIZED WATER-IN-OIL EMULSIONS

This is a continuation of application Ser. No. 888,938 filed Mar. 22, 1978 which is a continuation-in-part of application Ser. No. 852,147 filed Nov. 16, 1977, both now abandoned.

BACKGROUND OF THE INVENTION

This invention relates to an improved vehicle for topical applied medicinal or cosmetic products. The vehicle is a stable water-in-oil emulsion which is not significantly diluted by perspiration, rain, showering, or swimming. The vehicle of this invention then is suitable for application of a medicinal composition to alleviate skin disorders associated with inflammation, for example, or for incorporating a sun protective agent to prevent the harmful effects of sunlight on the human skin.

Two types of emulsions are commonly known. These emulsions are either the oil-in-water (o/w) or water-in-oil emulsions (w/o). In the former, water is the external phase or the dispersion medium, and in the latter, oil is the external phase with water being the dispersed phase. Oil-in-water emulsions are water washable and are the vehicles used in most cosmetic and pharmaceutical products.

In contrast, water-in-oil emulsions are water non-washable vehicles which are not widely used in either cosmetic or pharmaceutical products. Water-in-oil emulsions possess two distinct properties. These properties are substantiation and occlusion after application onto the skin. Therefore a water-in-oil cream is not significantly diluted by perspiration. In addition, application of a water-in-oil emulsion to skin disorders such as dry skin or inflammatory skin, will result in a protective or occlusive effect on the lesions.

There are two major problems associated with water-in-oil emulsions however. In the past, these emulsions have not exhibited storage stability, and when topically applied, these emulsions exhibit a greasy feeling on the skin. Known past attempts at formulating water-in-oil emulsion vehicles have been unsuccessful in both eliminating a greasy feeling and in providing realistic storage stability.

In water-in-oil emulsions, where water is the internal phase, theoretically, there is a maximum limit on the water content and a minimum requirement for the oil concentration. For example, in non-ionic water-in-oil emulsions, the theoretical maximum water content is 74%. In actuality, water content, normally, is 50% or less. Even at this concentration, the formulation of a true water-in-oil emulsion that is thermally stable, e.g. at 50° C. for an extended period of time, is a great challenge.

In an ionic water-in-oil emulsion, the water content is usually 35% or less. For example, one of the most well known ionic water-in-oil emulsions is the beeswax-borax cream which consists of the following ingredients: sorbitan sesquioleate, 1 part; mineral oil, 50 parts; beeswax, 10 parts; lanolin, 3.1 parts; borax, 0.7 parts; and water, 35.2 parts. This cream, due to the lanolin and high mineral oil content, feels quite greasy to the touch. In addition, this emulsion breaks down after storage after about one month at 50° C. Furthermore, borax is not a risk-free substance. Therefore, there exists a need for a more stable formulation that is safe to use.

In formulating water-in-oil emulsions, one of the most frequently observed difficulties is the appearance of a transparent oil layer at the surface. It has been suggested that the addition of small amounts of polyvalent metal soaps such as magnesium sulfate in a concentration of 0.1 to 0.2% to the emulsion during preparation will help resist this instability. However, under test conditions, neither magnesium sulfate, nor compounds such as magnesium chloride, aluminum oxide, aluminum hydroxide, zinc oxide, zinc hydroxide, ferric sulfate, ferric hydroxide, basic calcium phosphate, or calcium carbonate were effective in stabilizing water-in-oil emulsions under the test conditions to be hereinafter described.

A recent report by P. Thau entitled "Stabilization of Water-in oil Emulsion by in situ Formation of Calcium Soaps" Cosmetics and Toiletries 92 57–59, (1977) indicates that calcium saccharate can enhance the thermal stability of water-in-oil emulsions. Calcium saccharate is a complex mixture of 2 moles of sucrose with 1 mole of calcium oxide. It has been speculated that calcium saccharate enhances the stability of water-in-oil emulsions by allowing the in situ formulation of a high concentration of calcium stearate or calcium oleate. Calcium hydroxide has also been noted to exert a similar effect after being mixed with sucrose or other sugars.

However, it has been discovered that the in situ formation of soaps such as calcium stearate or sodium stearate does not enhance the thermal stability of water-in-oil emulsions. On the contrary, the above soaps appeared to exert an unstabilizing influence on water-in-oil emulsions. Water-in-oil emulsions were formulated for testing between stearic acid and each of the following compounds: calcium hydroxide, monobasic sodium phosphate, dibasic sodium phosphate, sodium silicate, and calcium gluconate. These emulsions were then tested for stability at 50° C. and in each instance, the emulsion destabilized and broke.

It has been discovered however, that water-in-oil emulsions may be successfully stabilized even at high water concentrations by the addition of a small concentration of magnesium oxide or magnesium hydroxide. According to this invention, it has been discovered that stearic acid or other fatty acids are not required in emulsion formulations, and special equipment or mixing procedures are also not necessary in order to prepare stable emulsions. Ordinary, commercially available mixing equipment is sufficient for preparation of the water-in-oil emulsions of this invention.

The therapeutic use of magnesium hydroxide for either internal or topical application is the subject of several prior U.S. Patents. For example, in U.S. Pat. No. 1,384,460 and emulsion, for internal use, of mineral oil and milk of magnesia is described. In addition, in U.S. Pat. Nos. 1,999,160 and 1,999,161, the topical application of magnesium hydroxide in a skin-cleansing cream containing from 0.5 to 6% magnesium hydroxide is described. The skin cleansing cream, however, utilizes beeswax and borax as an emulsifying agent and incorporates magnesium hydroxide as an astringent which is sufficiently alkaline to neutralize acid excretions found on the skin.

In addition, U.S. Pat. No. 2,414,024 describes an oil-in-water emulsion utilizing magnesium hydroxide. This patent, however, describes an emulsion of increased stability due to the presence of an alkaline earth salt of a cyclic or substituted cyclic acid in addition to a magnesium hydroxide suspension therein.

In accordance with the present invention, however, magnesium oxide or magnesium hydroxide is incorporated into an emulsion composition during the preparation thereof. The concentration of magnesium hydroxide or magnesium oxide may vary from 0.02 to 2% by weight of the total composition, and the preferred concentration range is from 0.1 to 0.5% thereof. The magnesium oxide or magnesium hydroxide stabilizing agent may be incorporated in either the oil phase or the aqueous phase before mixing or may be added to the emulsion after mixing.

The oil phase may consist of one or more well known products such as petrolatum, mineral oil, beeswax, isopropyl myristate, isopropyl palmitate, squalene, squalane, tocopheryl acetate, lanolin, wax, spermaceti, hydrogenated vegetable oil, chicken oil, or suet fat. The emulsifier may be a compound such as sorbitan monooleate, sorbitan sesquioleate, or sorbitan trioleate. A combination of ingredients in the oil phase may utilize each of the foregoing ingredients in a range of from 0 to 20% by weight of the total composition, but the preferred concentration range is up to 10% thereof.

The aqueous phase may consist of water, sorbitol, propylene glycol, 1,3-butanediol, and glycerin. The concentration of water may range up to 70% by weight of the total composition with the preferred concentration range being from 30 to 60% thereof. The concentration of sorbitol, propylene glycol, 1,3-butanediol, or glycerin may range up to 10% by weight of the total composition, with the preferred concentration range being from 2 to 5% thereof.

In preparing the water-in-oil emulsions of this invention, the oil phase and the aqueous phase preferably are separately heated to 75°-80° C., and the aqueous phase slowly poured into the oil phase with agitation. Agitation is continued until the mixture congeals. Any preservative or fragrance desired may be added to the water-in-oil emulsion without affecting its stability. After the emulsion is formed, other cosmetic ingredients or pharmaceutical drugs may be incorporated therein. For example, hydrocortisone has been incorporated in a water-in-oil emulsion of the present invention at a concentration of 1% by weight of the total composition.

It has been established in extensive tests that magnesium oxide or magnesium hydroxide in a concentration of from 0.02 to 2% and preferably from 0.1 to 0.5% thereof stabilizes a water-in-oil emulsion. Emulsions of this invention have been successfully stored for two months at 50° C., and have been shown to be stable after freezing and thawing. Both therapeutic and cosmetic agents have been incorporated in emulsions of this invention successfully. As noted above, a hydrocortisone water-in-oil emulsion of this invention was formulated. This composition was tested on humans having eczema and psoriasis and was proven to be therapeutically effective when applied on a daily basis to cause within about one week's time a return of the affected area to normal skin condition. Furthermore, the sun-screen agent p-aminobenzoic acid or its ester has been incorporated in water-in-oil emulsions of this invention in concentrations of from 1 to 10% and have proven effective in preventing harmful damage to the skin caused by sunlight.

It has also been established in extensive tests that the emulsions of this invention when used as a vehicle for therapeutic compositions useful in treating inflammatory skin diseases by topical application produce a therapeutically superior medicinal composition. The emulsions of this invention have been shown to improve the ability of such compounds as hydrocortisone, hydrocortisone 17-valerate, triamcinolone acetonide, 6-aminonicotinamide, and 6-aminonicotinic acid methyl ester to alleviate the symptoms of inflammatory skin diseases such as psoriasis, dermatitis, and eczema.

Inflammatory skin diseases are clinically characterized by redness, swelling and heat, and may or may not be accompanied by an itching sensation or pain. In clinical treatment of most inflammatory skin disorders, including psoriasis, dermatitis and eczema, tests have shown that the most prompt relief and healing is obtained with the medicinal ingredient incorporated in a vehicle containing water which is applied to the skin, and the area effected covered with an occlusive dressing such as a plastic film. A vehicle then most useful in the treatment of inflammatory skin diseases optimally possess two distinct properties, (A) providing moisture, and (B) providing occlusion.

Since an oil-in-water (O/W) emulsion has water in the external phase and oil as a dispersion medium, use of this type of emulsion in treatment of inflammatory skin diseases provides only moisture, but not occlusion. In contrast, petrolatum, provides occlusion, but no moisture.

While it is not known with certainty, it is believed that enhanced curing achieved with the water-in-oil (W/O) emulsion of the present invention lies in the fact that such a vehicle provides both moisture and occlusion. Oil is the external phase with water being the dispersed phase. Therefore, the water-in-oil emulsion of the present invention provides both moisture and occlusion and the tests, as will be subsequently described, have shown such an emulsion to be more efficacious than the same concentration of active ingredient in an oil-in-water emulsion such as hydrophilic ointment, or in petrolatum.

Accordingly, it is an object of this invention to provide a stabilizing agent for water-in-oil emulsions useful as vehicles for cosmetics or for medicinal applications.

It is another object of this invention to incorporate magnesium oxide or magnesium hydroxide in conventional water-in-oil vehicles to stabilize said vehicles.

It is another object of this invention to provide a medicinal composition containing a pharmaceutical compound in a stable water-in-oil emulsion which, when topically applied, will alleviate symptoms of inflammatory diseases.

It is still another object of this invention to provide a cosmetic composition containing a sun-protective agent in a stable water-in-oil emulsion which, when topically applied, will reliably prevent damage to the skin by sunlight.

It is still another object of this invention to provide a method for stabilizing water-in-oil emulsions with magnesium oxide or magnesium hydroxide.

These and other objections will become readily apparent with reference to the following description.

The following are illustrative examples of formulations of water-in-oil emulsions useful as vehicles for topical application according to this invention. It should be understood that the following examples are illustrative only and not limitative of the invention. Therefore, any of the aforementioned wax, fat or oil compositions may be substituted according to the teachings of this invention in the following formulations.

EXAMPLE 1

A W/O emulsion containing 34% water may be formulated as follows:

Part A:
Sorbitan sesquioleate—2 gm
Petrolatum—10 gm
Mineral oil—20 gm
Beeswax—10 gm
Isopropyl palmitate—10 gm
Squalene—5 gm
Part B:
Water—34 ml
Sorbitol—3 gm
Propylene glycol—5 ml
Magnesium oxide—0.2 gm Heat Part A to 75° C. and heat Part B to 80° C. Add Part B slowly to Part A with agitation. Continue agitation until the mixture is congealed.

EXAMPLE 2

A W/O emulsion containing 44% water may be prepared as follows:
Part A:
Sorbitan sesquioleate—2 gm
Petrolatum—10 gm
Mineral oil—10 gm
Beeswax—10 gm
Isopropyl myristate—5 gm
Tocopheryl acetate—5 gm
Squalene—5 gm
Part B:
Water—44 ml
Sorbitol—3 gm
Propylene glycol—5 ml
Magnesium oxide—0.1 gm Heat Part A to 75° C. and heat Part B to 80° C. Add Part B slowly to Part A with agitation. Continue agitation until the mixture is congealed.

EXAMPLE 3

A W/O emulsion containing 50% water may be formulated as follows:
Part A:
Sorbitan sesquioleate—2 gm
Petrolatum—10 gm
Mineral oil—15 gm
Beeswax—7 gm
Isopropyl myristate—7 gm
Part B:
Water—50 ml
Sorbitol—3 gm
Propylene glycol—5 ml
Magnesium oxide—0.1 gm Heat Part A to 75° C. and heat Part B to 80° C. Add Part B slowly to Part A with agitation. Continue agitation until the mixture is congealed.

EXAMPLE 4

A W/O emulsion containing 60% water may be prepared as follows:
Part A:
Sorbitan sesquioleate—2 gm
Petrolatum—10 gm
Mineral oil—10 gm
Beeswax—5 gm
Isopropyl myristate—5 gm
Part B:
Water—60 ml
Propylene glycol—5 ml
Sorbitol—3 gm
Magnesium oxide—0.2 gm Heat Part A to 75° C. and heat Part B to 80° C. Add Part B slowly to Part A with agitation. Continue agitation until the mixture is congealed.

EXAMPLE 5

A W/O emulsion using a different emulsifier may be prepared as follows:
Part A:
Sorbitan monooleate—2 gm
Petrolatum—10 gm
Mineral oil—20 gm
Beeswax—10 gm
Isopropyl palmitate—10 gm
Part B:
Water—40 ml
Sorbitol—3 gm
Propylene glycol—5 ml
Magnesium oxide—0.2 gm Heat Part A to 75° C. and heat Part B to 80° C. Add Part B slowly to Part A with agitation. Continue agitation until the mixture is congealed.

EXAMPLE 6

A W/O emulsion using another different emulsifier may be prepared as follows:
Part A:
Sorbitan trioleate—2 gm
Petrolatum—10 gm
Mineral oil—20 gm
Beeswax—10 gm
Isopropyl myristate—10 gm
Part B:
Water—40 ml
Sorbitol—3 gm
Propylene glycol—5 ml
Magnesium oxide—0.2 gm Heat Part A to 75° C. and heat Part B to 80° C. Add Part B slowly to Part A with agitation. Continue agitation until the mixture is congealed.

EXAMPLE 7

A W/O emulsion using another different emulsifier may be formulated as follows:
Part A:
Sorbitan monostearate—2 gm
Petrolatum—10 gm
Mineral oil—20 gm
Beeswax—10 gm
Isopropyl myristate—10 gm
Part B:
Water—40 ml
Sorbitol—3 gm
Propylene glycol—5 ml
Magnesium oxide—0.2 gm Heat Part A to 75° C. and heat Part B to 80° C. Add Part B slowly to Part A with agitation. Continue agitation until the mixture is congealed.

EXAMPLE 8

A W/O emulsion using magnesium hydroxide as a stabilizer may be formulated as follows:
Part A:
Sorbitan sesquioleate—2 gm
Petrolatum—15 gm
Mineral oil—15 gm
Beeswax—10 gm
Isopropyl myristate—10 gm
Squalene—5 gm Part B:
Water—34 ml
Sorbitol—3 gm
Propylene glycol—5 ml
Magnesium hydroxide—0.2 gm Heat Part A to 75° C. and heat Part B to 80° C. Add Part B slowly to Part A with agitation. Continue agitation until the mixture is congealed

EXAMPLE 9

A W/O emulsion using magnesium hydroxide as a stabilizer and glycerin as a polyol may be prepared as follows:
Part A:
Sorbitan trioleate—2 gm
Petrolatum—15 gm
Mineral oil—15 gm
Beeswax—10 gm
Isopropyl palmitate—10 gm
Squalene—5 gm
Part B:
Water—34 ml
Sorbitol—3 gm
Glycerin—5 ml
Magnesium hydroxide—0.2 gm Heat Part A to 75° C. and heat Part B to 80° C. Add Part B slowly to Part A with agitation. Continue agitation until the mixture is congealed.

EXAMPLE 10

A W/O emulsion using magnesium oxide as a stabilizer may be formulated as follows:
Part A:
Sorbitan sesquioleate—2 gm
Petrolatum—15 gm
Mineral oil—15 gm
Beeswax—10 gm
Isopropyl myristate—10 gm
Squalene—5 gm
Part B:
Water—34 ml
Dextrose—3 gm
Propylene glycol—5 ml
Magnesium oxide—0.2 gm Heat Part A to 75° C. and heat Part B to 80° C. Add Part B slowly to Part A with agitation. Continue agitation until the mixture is congealed.

EXAMPLE 11

Hydrocortisone 1% in a W/O emulsion may be prepared as follows:

Hydrocortisone, USP, 1 gm is directly mixed with a W/O cream, 99 gm prepared according to Example 1. The mixing is continued until a uniform consistency is obtained.

EXAMPLE 12

P-Aminobenzoic acid 5% in a W/O emulsion may be prepared as follows:

P-Aminobenzoic acid 5 gm is directly mixed with a W/O cream, 95 gm prepared according to Example 2. The mixing is continued until a uniform consistency is obtained.

EXAMPLE 13

A W/O emulsion containing no petrolatum may be formulated as follows:
Part A:
Sorbitan sesquioleate—2 gm
Mineral oil—10 gm
Beeswax—5 gm
Isopropyl myristate—5 gm
Tocopheryl acetate—2 gm
Squalene—3 gm
Suet fat—10 gm
Part B:
Water—55 ml
Sorbitol—3 gm
Propylene glycol—5 ml
Magnesium oxide—0.2 gm Heat Part A to 75° C. and heat Part B to 80° C. Add Part B slowly to Part A with agitation. Continue agitation until the mixture is congealed.

EXAMPLE 14

A W/O emulsion containing neither petrolatum nor mineral oil may be formulated as follows:
Part A:
Sorbitan sesquioleate—2 gm
Beeswax—5 gm
Isopropyl myristate—10 gm
Suet fat—10 gm
Chicken fat—5 gm
Part B:
Water—60 ml
Sorbitol—3 gm
Propylene glycol—5 ml
Magnesium oxide—0.2 gm Heat Part A to 75° C. and heat Part B to 80° C. Add Part B slowly to Part A with agitation. Continue agitation until the mixture is congealed.

TEST RESULTS

The emulsions of this invention were tested for instability by evaluating creaming, sedimentation, inversion, transparent oil formation, and phase separation. It has been shown that an increase in the storage temperature of 10° C. will double the speed of reaction. Therefore, storage of a water-in-oil emulsion for three months at 50° C. would correspond to a shelf-life storage period of two years at 20° C.

Each of the compositions formulated according to the above examples were tested for storage stability in two-ounce transparent bottles and jars. The bottles and jars were kept at a temperature of 50° C. for an extended period of time of at least two months. In each case, the emulsions prepared were stable when evaluated according to the above criteria for a period of at least two months.

The emulsions of this invention were also evaluated by a freeze-thaw test. Each of the emulsions as formulated in the foregoing examples, were subjected to freezing at a temperature of −20° C. and subsequent thawing to room temperature. In each instance, the water-in-oil emulsions of this invention were found to be stable as determined by the above criteria.

In order to evaluate the suitability of the emulsions of this invention for use with the medicinal compositions, 11 patients having psoriasis, and 6 patients having eczema were tested with a 1% hydrocortisone cream prepared according to Example 11, and with a hydrocortisone in hydrophilic ointment at a concentration of 1%. Test areas were kept to minimal size convenient for topical application: circles 4 cm in diameter demarcated with a plastic ring of that size inked on a stamp pad. The medicinal creams were topically applied by the patient in an amount sufficient to cover the test site. Applications were made usually three times daily without occlusive dressings. Test intervals did not exceed two weeks, and applications were discontinued at any time when resolution of the lesion on the test area was clinically judged to be complete.

It was discovered that the hydrocortisone 1% cream of Example 11 was markedly effective in the treatment of the six patients with eczema. Complete resolution of the test sites treated with this medicinal composition were obtained within a one-week period of time. Only a moderate improvement was found in the test sites treated with hydrocortisone 1% in hydrophilic ointment.

In ten of the eleven psoriatic patients tested with hydrocortisone 1% cream prepared according to Example 11 a substantial to complete clearing of the test sites was achieved within one to two weeks. Under the same circumstances, hydrocortisone 1% in hydrophilic ointment afforded only marginal to moderate improvement in all patients tested.

In addition, the cosmetic use of the water-in-oil emulsions of this invention was tested utilizing p-aminobenzoic acid at a 5% concentration in a water-in-oil emulsion prepared according to Example 12. Human volunteers topically applied the composition. It was found that perspiration, sweating or swimming did not diminish the sun protecting ability of p-aminobenzoic acid when formulated according to Example 12.

Results of Clinical Efficacy Tests

Clinical tests were conducted to evaluate the water-in-oil emulsions of this invention to determine whether said emulsions increased the efficacy of known therapeutic agents for the treatment of inflammatory skin diseases. In each instance, identical concentrations of the agent in the water-in-oil emulsion of this invention, hydrophilic ointment, and petrolatum were evaluated. The following are the results of these tests.

Hydrocortisone

Therapeutic compositions containing 0.2% and 1% hydrocortisone in (a) hydrophilic ointment, USP, (b) petrolatum and (c) W/O emulsion of this invention were topically administered to 11 patients having psoriasis and 6 patients having eczema. Test areas were kept to minimal size convenient for topical application: circles 4 cm in diameter demarcated with a plastic ring of that size inked on a stamp pad. The medicinal creams or ointments were topically applied by the patient in an amount sufficient to cover the test site. Applications were made three times daily and without occlusive dressings. Test periods did not exceed two weeks, and applications were discontinued at any time when resolution of the lesion on the test area was clinically judged to be complete.

It was discovered that hydrocortisone 0.2% and 1% in W/O emulsion of the present invention were much more efficacious than the same concentration of hydrocortisone in hydrophilic ointment or petrolatum in the treatment of patients having the inflammatory disorders; psoriasis and eczema.

Complete resolution of the test sites treated with hydrocortisone 0.2% or 1% in W/O emulsion of the present invention was obtained within a one-week period of time in all six patients having eczema. Only a moderate improvement was found in the test sites treated with hydrocortisone 0.2% or 1% in hydrophilic ointment or in petrolatum.

In ten of the eleven psoriatic patients tested with hydrocortisone 0.2% or 1% in W/O emulsion of the present invention a substantial to complete clearing of the test sites was achieved within one to two weeks. Under the same circumstances, hydrocortisone 0.2% or 1% in hydrophilic ointment or petrolatum afforded only marginal to moderate improvement in all patients tested.

Hydrocortisone 17-valerate

Medicinal compositions containing 0.2% and 1% hydrocortisone 17-valerate in (a) hydrophilic ointment, USP, (b) petrolatum and (c) W/O emulsion of this invention were topically administered to 9 patients having psoriasis, 5 patients having eczema and 4 patients having Sezary syndrome, a variant of the skin cancer known as mycosis fungoides.

The method and schedule of topical application were the same as described above.

It was found that hydrocortisone 17-valerate 0.2% or 1% in W/O emulsion of the present invention was much more efficacious than the same concentration of hydrocortisone 17-valerate in hydrophilic ointment or petrolatum in the treatment of patients having the above inflammatory skin diseases.

Complete resolution of the test sites treated with hydrocortisone 17-valerate 0.2% or 1% in W/O emulsion of the present invention was found to occur within one to two week period of time in all nine patients having psoriasis and in all five patients having eczema. Only a moderate improvement was obtained in the test sites treated with hydrocortisone 17-valerate 0.2% or 1% in hydrophilic ointment or in petrolatum.

In all four patients having Sezary syndrome a substantial improvement of the test sites treated with hydrocortisone 17-valerate 0.2% or 1% in W/O emulsions of the present invention was achieved within one to two weeks. Under the same circumstances, hydrocortisone 17-valerate 0.2% or 1% hydrophilic ointment or in petrolatum afforded only marginal to moderate improvement in all patients tested.

Triamcinolone acetonide

Therapeutic compositions containing 0.02% triamcinolone acetonide in (a) hydrophilic ointment, USP, (b) petrolatum and (c) W/O emulsion of this invention were topically administered to 14 patients having psoriasis.

The method and schedule of topical application were the same as described above.

It was found that triamcinolone acetonide 0.02% in W/O emulsion of the present invention was much superior to the same concentration of triamcinolone acetonide in hydrophilic ointment or petrolatum in the treatment of psoriatic patients.

Complete clearing of the test sites treated with triamcinolone acetonide 0.02% in W/O emulsion of the present invention occurred within one week period of time in all fourteen patients having psoriasis. Under the same circumstances, only a slight to moderate improvement was obtained in the test sites treated with triamcinolone acetonide 0.02% in hydrophilic ointment or in petrolatum.

6-Aminonicotinamide

Medicinal compositions containing 0.1% 6-aminonicotinamide in (a) hydrophilic ointment, USP, (b) petrolatum and (c) W/O emulsion of this invention were prepared as follows.

6-Aminonicotinamide crystals were converted to a powder form (200-400 mesh) with a ball-mill machine. Powdered 6-aminonicotinamide 0.1 gram was directly admixed with 99.9 grams of (a) hydrophilic ointment, USP, (b) petrolatum or (c) W/O emulsion of the present invention.

The therapeutic compositions as described in our U.S. Pat. No. 4,067,975 thus formulated were topically administered to 22 patients having psoriasis. The method and schedule of topical application was the same as described above.

It was discovered that 6-aminonicotinamide 0.1% in W/O emulsion of the present invention was superior to the same concentration of 6-aminonicotinamide in hydrophilic ointment or petrolatum in the treatment of patients having psoriasis.

Complete resolution of the test sites treated with 6-aminonicotinamide 0.1% in W/O enulsion of the present invention was obtained within a one week period of time in 21 out of 22 psoriatic patients tested. Under the said circumstances, although moderate to substantial improvement occurred in the test sites treated with 6-aminonicotinamide 0.1% in hydrophilic ointment or in petrolatum, the degree of improvement was less than that achieved with 6-aminonicotinamide 0.1% in W/O emulsion of the present invention.

2-Aminonicotinic acid methyl ester

Medicinal compositions containing 0.2% 6-aminonicotinic acid methyl ester in (a) hydrophilic ointment, USP, (b) petrolatum and (c) W/O emulsion of this invention was prepared as follows.

6-Aminonicotinic acid methyl ester 0.2 gram was dissolved in 5 ml of anhydrous ethanol and the solution was admixed with 95 grams of (a) hydrophilic ointment, (b) petrolatum or (c) W/O emulsion of the present invention.

The therapeutic compositions as described in our copending U.S. Patent Application Ser. No. 715,131, filed Aug. 17, 1976, thus prepared were topically administered to 22 patients having psoriasis. The method and schedule of topical application were the same as described above.

It was discovered that 6-aminonicotinic acid methyl ester 0.2% in W/O emulsion of the present invention was much more efficacious than the same concentration of 6-aminonicotinic acid methyl ester in hydrophilic ointment or petrolatum in the treatment of patients having psoriasis.

Complete clearing of the test sites treated with 6-aminonicotinic acid methyl ester 0.2% in W/O emulsion of the present invention was found to occur within a two week period of time in 20 out of 22 psoriatic patients tested. Under the same circumstances only a moderate to substantial improvement was found in the test sites treated with 6-aminonicotinic acid methyl ester 0.2% in hydrophilic ointment or in petrolatum.

It should be emphasized that the aforementioned tests are not intended to attribute therapeutic value to the emulsions of this invention, but rather to indicate that efficacy of a therapeutic agent for the treatment of inflammatory skin conditions is markedly improved by utilizing the water-in-oil emulsion of this invention as a vehicle therefor. As noted above, use of a water containing vehicle, and an occlusive barrier dressing such as plastic sheet to cover the involved area treated is the most effective means for applying the therapeutic agent. Use of a plastic sheet type occlusive barrier however is not always feasible or possible. In the absence thereof, however, as shown above, clinical tests have established that the emulsion of the instant invention improves the efficacy of the therapeutic agent substantially when compared to convention vehicles, petrolatum or hydrophilic ointment, USP.

In summary then, it has been discovered that stable water-in-oil emulsions may be prepared according to this invention by utilizing magnesium hydroxide or magnesium oxide as a stabilizing agent. The emulsions of this invention, then, are suitable for use as a vehicle for the topical application of medicinal compounds or cosmetics and provide an occlusive effect without a disagreeable feeling of greasiness. The stabilizing agent of this invention may be incorporated in either the oil phase or the water phase prior to mixing, or may be incorporated into the emulsion after mixing. By utilizing the stabilizing agent of this invention, fatty acids, soaps, and the like, borax, or other well known stabilizing or agents are not necessary. The emulsions of this invention, then, have been proven to be stable for storage for extended periods of time and against freezing and thawing.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed and desired to be secured by United States Letters Patent is:

1. A method for stabilizing a water-in-oil emulsion for topical application to the human body, so that said emulsion will be stable when stored for two months and stable when subjected to freezing with subsequent thawing to room temperature comprising: admixing an oil base dispersion medium, an emulsifying agent, and a water based, aqueous dispersed phase, and a stabilizing effective amount of up to about 2%, by weight, of a member selected from the group consisting of magnesium hydroxide and magnesium oxide.

2. The method of claim 1 wherein said stabilizing agent is present in a concentration of from 0.1 to 0.5%.

3. The method of claim 1 wherein said agent is incorporated in the aqueous phase before said aqueous phase and dispersion medium are mixed.

4. The method of claim 1 wherein said agent is incorporated in the dispersion medium before said medium and the aqueous phase are mixed.

5. The method of claim 1 wherein said agent is admixed directly with said emulsion.

6. A method for producing a stable water-in-oil emulsion comprising:

providing a dispersion medium consisting of a plurality of members selected from the group consisting of petrolatum, mineral oil, beeswax, isopropyl myristate, isopropyl palmitate, squalene, squalane, tocopheryl acetate, lanolin, wax, spermaceti, hydrogenated vegetable oil, chicken oil, and suet fat;
admixing an emulsifier therewith selected from the group consisting of sorbitan monooleate, sorbitan sesquioleate, and sorbitan trioleate;
providing an aqueous phase consisting of a plurality of members selected from the group consisting of water, sorbitol, propylene glycol, 1,3-butanediol, and glycerin;
admixing from 0.2 to 2% of a stabilizing agent selected from the group consisting of magnesium hydroxide and magnesium oxide with said aqueous phase;
separately heating said phases to 75°–80° C.;
pouring the aqueous phase into the dispersion phase with agitation until the mixture congeals.

7. A method for producing a stable water-in-oil emulsion comprising:
providing a dispersion medium consisting of a plurality of members selected from the group consisting of petrolatum, mineral oil, beeswax, isopropyl myristate, isopropyl palmitate, squalene, squalane, tocopheryl acetate, lanolin, wax spermaceti, hydrogenated vegetable oil, chicken oil, and suet fat;
admixing an emulsifier therewith selected from the group consisting of sorbitan monooleate, sorbitan sesquioleate, and sorbitan trioleate;
providing an aqueous phase consisting of a plurality of members selected from the group consisting of water, sorbitol, propylene glycol, 1,3-butanediol, and glycerin;
admixing from 0.2 to 2% of a stabilizing agent selected from the group consisting of magnesium hydroxide and magnesium oxide with said dispersion medium;
separately heating said aqueous phase and said dispersion medium to 75°–80° C.;
pouring said aqueous phase into said dispersion medium with agitation until the mixture congeals.

8. A method for producing a stable water-in-oil emulsion comprising:
providing a dispersion medium consisting of a plurality of members selected from the group consisting of petrolatum, mineral oil, beeswax, isopropyl myristate, isopropyl palmitate, squalene, squalane, tocopheryl acetate, lanolin, wax, spermaceti, hydrogenated vegetable oil, chicken oil, and suet fat;
admixing an emulsifier with said dispersion medium selected from the group consisting of sorbitan monooleate, sorbitan sesquioleate, and sorbitan trioleate;
providing an aqueous phase consisting of a plurality of members selected from the group consisting of water, sorbitol, propylene glycol, 1,3-butanediol, and glycerin;
separately heating said phases to 75°–80° C.;
pouring the aqueous phase into the dispersion medium with agitation until the mixture congeals;
admixing from 0.2 to 2% of a stabilizing agent selected from the group consisting of magnesium hydroxide and magnesium oxide with said mixture.

9. The method of claim 6 wherein said stabilizing agent is present in a concentration of 0.1 to 0.5%.

10. The method of claim 7 wherein said stabilizing agent is present in a concentration of 0.1 to 0.5%.

11. The method of claim 8 wherein said stabilizing agent is present in a concentration of 0.1 to 0.5%.

12. The method of claim 6 wherein water is present in from 30 to 60%, by weight, of said emulsion.

13. The method of claim 7 wherein water is present in a concentration of from 30 to 60%, by weight, of the total emulsion.

14. The method of claim 8 wherein water is present in a concentration of from 30 to 60%, by weight, of the total emulsion.

15. A stable water-in-oil emulsion for use as a vehicle for topical application to the human body with cosmetic or medicinal compositions comprising:
an oil phase dispersion medium containing a plurality of members selected from the group consisting of petrolatum, mineral oil, beeswax, isopropyl myristate, isopropyl palmitate, squalene, squalane, tocopheryl acetate, lanolin, wax, spermaceti, hydrogenated vegetable oil, chicken oil, and suet fat;
an emulsifier admixed therein selected from the group consisting of sorbitan monooleate, sorbitan sesquioleate, and sorbitan trioleate, and sorbitan monostearate;
an aqueous phase dispersed therein consisting of from 30 to 70% by weight of the total composition, of a plurality of members selected from the group consisting of water, sorbitol, propylene glycol, 1,3-butanediol, dextrose, and glycerin; and
a stabilizing agent dispersed throughout said emulsion selected from the group consisting of magnesium oxide and magnesium hydroxide present in a concentration of from 0.02 to 2% by weight of the total composition.

16. The emulsion of claim 15 wherein the stabilizing agent is present in a concentration of from 0.1 to 0.5%.

17. The emulsion of claim 15 wherein water is present in a concentration of from 30 to 60% by weight of the total composition.

18. The stabilized water-in-oil emulsion of claim 15 further comprising:
an oil phase dispersion medium comprising a mixture 2 parts of an emulsifying agent sorbitan sesquioleate; 10 parts petrolatum; 20 parts mineral oil; 10 parts beeswax; 10 parts isopropyl palmitate; and 5 parts squalene; and an aqueous phase dispersed therein comprising 34 parts water, 3 parts sorbitol, and 5 parts propylene glycol, said emulsion stabilized by the admixing of 0.2 parts magnesium oxide therein.

19. The stabilized water-in-oil emulsion of claim 15 further comprising:
an oil phase dispersion medium comprising a mixture of 2 parts of an emulsifying agent sorbitan sesquioleate; 10 parts petrolatum; 10 parts mineral oil; 10 parts beeswax; 5 parts isopropyl myristate; 5 parts tocopheryl acetate; 5 parts squalene; and an aqueous phase dispersed therein comprisng 44 parts water, 3 parts sorbitol, 5 parts propylene glycol, said emulsion stabilized by the dispersion of 0.1 parts magnesium oxide therein.

20. The stabilized water-in-oil emulsion of claim 15 further comprising:
an oil phase dispersion medium comprising a mixture of 2 parts sorbitan sesquioleate; 10 parts petrolatum; 15 parts mineral oil; 7 parts beeswax; 7 parts isopropyl myristate; and an aqueous phase dispersed therein comprising 50 parts water, 3 parts sorbitol, 5 parts propylene glycol, said emulsion stabilized by the dispersion of 0.1 parts magnesium oxide therein.

21. The stabilized water-in-oil emulsion of claim 15 further comprising:

an oil phase dispersion medium comprising a mixture of 2 parts sorbitan sesquioleate, 10 parts petrolatum, 10 parts mineral oil, 5 parts beeswax, 5 parts isopropyl myristate; and an aqueous phase dispersed therein comprising 60 parts water, 5 parts propylene glycol, 3 parts sorbitol, said emulsion stabilized by the dispersion of 0.2 parts magnesium oxide therein.

22. The stabilized water-in-oil emulsion of claim 15 further comprising:
an oil phase dispersion medium comprising a mixture of 2 parts sorbitan monooleate, 10 parts petrolatum, 20 parts mineral oil, 10 parts beeswax, 10 parts isopropyl palmitate; and an aqueous phase dispersed therein comprising 40 parts water, 3 parts sorbitol, 5 parts propylene glycol, said emulsion stabilized by the dispersion of 0.2 parts magnesium oxide therein.

23. The stabilized water-in-oil emulsion of claim 15 further comprising:
an oil phase dispersion medium comprising a mixture of 2 parts sorbitan trioleate, 10 parts petrolatum, 20 parts mineral oil, 10 parts beeswax, 10 parts isopropyl myristate; and an aqueous phase dispersed therein comprising 40 part water, 3 parts sorbitol, 5 parts propylene glycol, said emulsion stabilized by the dispersion of 0.2 parts magnesium oxide therein.

24. The stabilized water-in-oil emulsion of claim 15 further comprising:
an oil phase dispersion medium comprising a mixture of 2 parts sorbitan monostearate, 10 parts petrolatum, 20 parts mineral oil, 10 parts beeswax, 10 parts isopropyl myristate; and an aqueous phase dispersed therein comprising 40 parts water, 3 parts sorbitol, 5 parts propylene glycol, said emulsion stabilized by the dispersion of 0.2 parts magnesium oxide therein.

25. The stabilized water-in-oil emulsion of claim 15 further comprising:
an oil phase dispersion medium comprising a mixture of 2 parts sorbitan sesquioleate, 15 parts petrolatum, 15 parts mineral oil, 10 parts beeswax, 10 parts isopropyl myristate, 5 parts squalene; and an aqueous phase dispersed therein comprising 34 parts water, 3 parts sorbitol, 5 parts propylene glycol, said emulsion stabilized by the dispersion of 0.2 parts magnesium oxide therein.

26. The stabilized water-in-oil emulsion of claim 15 further comprising:
an oil phase dispersion medium comprising a mixture of 2 parts sorbitan trioleate, 15 parts petrolatum, 15 parts mineral oil, 10 parts beeswax, 10 parts isopropyl palmitate, 5 parts squalene; and an aqueous phase dispersed therein comprising 34 parts water, 3 parts sorbitol, 5 parts glycerin, said emulsion stabilized by the dispersion of 0.2 parts magnesium oxide therein.

27. The stabilized water-in-oil emulsion of claim 15 further comprising:
an oil phase dispersion medium comprising a mixture of 2 parts sorbitan sesquioleate, 5 parts petrolatum, 15 parts mineral oil, 10 parts beeswax, 10 parts isopropyl myristate, 5 parts squalene; and an aqueous phase dispersed therein comprising 34 parts water, 3 parts dextrose, 5 parts propylene glycol, said emulsion stabilized by the dispersion of 0.2 parts magnesium oxide therein.

28. The stabilized water-in-oil emulsion of claim 15 further comprising:
an oil phase dispersion medium comprising a mixture of 2 parts sorbitan sesquiolate, 10 parts mineral oil, 5 parts beeswax, 5 parts isopropyl myristate, 2 parts tocopheryl acetate, 3 parts squalene, 10 parts suet fat, and an aqueous phase dispersed therein comprising 55 parts water, 3 parts sorbitol, 5 parts propylene glycol, said emulsion stabilized by the dispersion of 0.2 parts magnesium oxide therein.

29. The stabilized water-in-oil emulsion of claim 15 further comprising:
an oil phase dispersion medium comprising a mixture of 2 parts sorbitan sesquioleate, 5 parts beeswax, 10 parts isopropyl myristate, 10 parts suet fat, 5 parts chicken fat, and an aqueous phase dispersed therein comprising 60 parts water, 3 parts sorbitol, 5 parts propylene glycol, said emulsion stabilized by the dispersion of 0.2 parts magnesium oxide therein.

30. A method for improving the efficacy of a medicinal compound selected from the group consisting of hydrocortisone, triamcinolone acetonide, and 6-aminonicotinamide which is effective to alleviate the symptoms of inflammatory skin diseases psoriasis and exzema by topical application to involved areas of the human body comprising:
providing a stabilized water-in-oil emulsion vehicle for said compound which is stable when stored for two months and stable when subjected to freezing with subsequent thawing to room temperature by admixing an oil based dispersion medium, an emulsifying agent, and a water based dispersion phase with a stabilizing agent present in a stabilizing effective amount of up to about 2%, by weight selected from the group consisting of magnesium hydroxide and magnesium oxide; whereby when an anti-inflammatory effective amount of said compound in said vehicle is topically applied to inflamed areas of the human body to alleviate the symptoms of said inflammation , said vehicle will provide a moist and occlusive covering thereof.

31. The method of claim 30 wherein said stabilizing agent is present in a concentration of from 0.1% to 0.5%.

32. The method of claim 30 wherein said dispersion medium consists of a plurality of members selected from the group consisting of petrolatum, mineral oil, beeswax, isopropyl myristate, isopropyl palmitate, squalene, squalane, tocopheryl acetate, lanolin, wax, spermaceti, hydrogenated vegetable oil, chicken oil, and suet fat.

33. The method of claim 32 wherein said emulsifier comprises a member selected from the group consisting of sorbitan monooleate, sorbitan sesquioleate, and sorbitan trioleate.

34. The method of claim 33 wherein aqueous phase consists of a plurality of members selected from the group consisting of water, sorbitol, propylene glycol, 1,3-butanediol, and glycerin.

* * * * *